(12) United States Patent
Thompson

(10) Patent No.: US 9,149,663 B2
(45) Date of Patent: Oct. 6, 2015

(54) ANTIPERSPIRANT EMULSION COMPOSITIONS AND PROCESSES FOR MAKING ANTIPERSPIRANT EMULSION COMPOSITIONS

(75) Inventor: Berea Thompson, Somerset, NJ (US)

(73) Assignee: The Dial Corporation, Scottsdale, AZ (US)

( * ) Notice: Subject to any disclaimer, the term of this patent is extended or adjusted under 35 U.S.C. 154(b) by 368 days.

(21) Appl. No.: 13/361,212

(22) Filed: Jan. 30, 2012

(65) Prior Publication Data

US 2013/0195785 A1    Aug. 1, 2013

(51) Int. Cl.
 *A61K 8/00* (2006.01)
 *A61Q 15/00* (2006.01)
 *A61K 8/06* (2006.01)

(52) U.S. Cl.
 CPC ............... *A61Q 15/00* (2013.01); *A61K 8/064* (2013.01); *A61K 2800/805* (2013.01)

(58) Field of Classification Search
 CPC .. A61Q 15/00; A61K 8/064; A61K 2800/805
 See application file for complete search history.

(56) References Cited

U.S. PATENT DOCUMENTS

| | | | |
|---|---|---|---|
| 5,891,425 A | 4/1999 | Bretzler et al. | |
| 6,143,284 A | 11/2000 | Bush et al. | |
| 6,231,842 B1 | 5/2001 | Scavone et al. | |
| 6,703,005 B2 | 3/2004 | Allan et al. | |
| 2008/0152608 A1* | 6/2008 | Cropper et al. | 424/66 |
| 2011/0038822 A1 | 2/2011 | Phipps et al. | |
| 2011/0038823 A1 | 2/2011 | Phipps et al. | |
| 2011/0038902 A1 | 2/2011 | Phipps et al. | |

OTHER PUBLICATIONS

PCT International Search Report (PCT/US2013/023630) dated May 15, 2013.

* cited by examiner

*Primary Examiner* — Lezah Roberts
*Assistant Examiner* — Nannette Holloman
(74) *Attorney, Agent, or Firm* — P. Scott Smith

(57) ABSTRACT

Processes for making an antiperspirant emulsion composition and antiperspirant emulsion compositions are provided herein. In an embodiment, a process for making an antiperspirant emulsion composition includes combining water and an antiperspirant active component to form a water phase. A hydrophobic carrier and a structurant are combined to form an oil phase. The structurant has a melting point above ambient temperature. The oil phase is heated to a first temperature of at least a melting point of the structurant that is disposed in the oil phase. The water phase and the heated oil phase are mixed to form the antiperspirant emulsion composition. The antiperspirant emulsion composition is cooled under continued mixing.

16 Claims, 1 Drawing Sheet

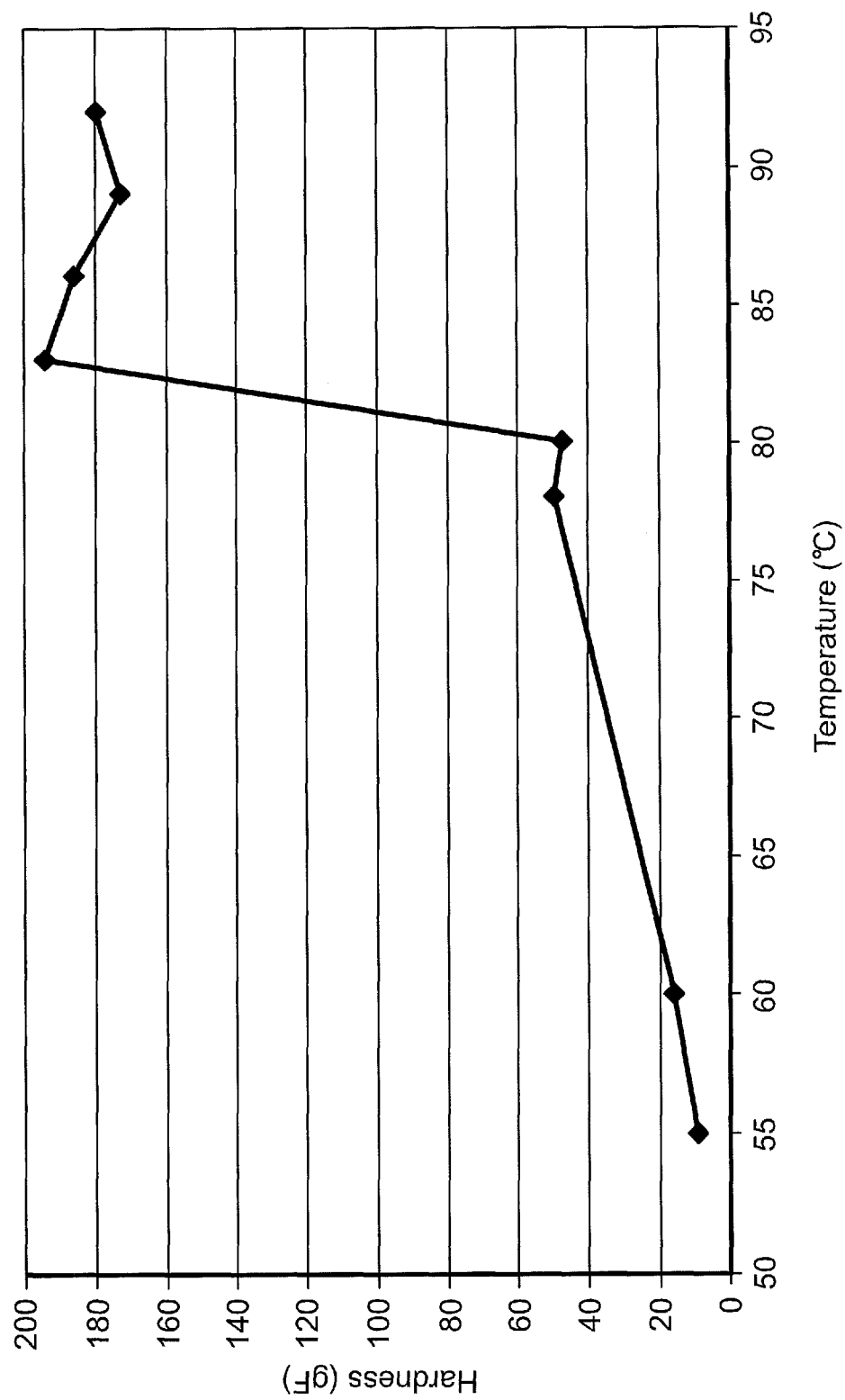

ANTIPERSPIRANT EMULSION COMPOSITIONS AND PROCESSES FOR MAKING ANTIPERSPIRANT EMULSION COMPOSITIONS

TECHNICAL FIELD

The present invention generally relates to antiperspirant emulsion compositions and processes for making antiperspirant emulsion compositions. More particularly, the present invention relates to antiperspirant emulsion compositions having a low hardness, processes for making antiperspirant emulsion compositions that enable hardness of the antiperspirant emulsion compositions to be modified, and antiperspirant emulsion compositions made by the process.

BACKGROUND

Antiperspirants are popular personal care products used to prevent or eliminate perspiration and body odor caused by perspiration. Antiperspirants typically prevent the secretion of perspiration by blocking or plugging perspiration-secreting glands, such as those located at the underarms. Antiperspirant sticks are desired by a large majority of the population because of the presence of antiperspirant active compounds that block or prevent the secretion of perspiration and the accompanying odors thereof and because of their ease of application. The antiperspirant composition is applied to the skin by swiping or rubbing the stick across the skin, typically of the underarm. However, antiperspirant users often are disappointed in the chalky, brittle, and/or crumbly application of the stick across the skin To reduce chalky, brittle, and/or crumbly application of the stick antiperspirant compositions across the skin, antiperspirant emulsion compositions that exhibit smooth application, with minimal crumbling or caking, have been developed. Such products typically include an emulsion of a water phase containing an active antiperspirant compound, such as an antiperspirant metal salt, and an oil phase containing, for example, a hydrophobic carrier, fragrances, structurants, and other additives.

For the antiperspirant emulsion compositions, solid stick antiperspirant emulsion compositions have been developed with varying hardness to meet particular preferences of consumers. However, formulating antiperspirant emulsion compositions to vary the hardness thereof generally requires formulary modification of the components of the antiperspirant emulsion compositions. For example, hardness of antiperspirant emulsion compositions may be influenced by various components including structurants, such as waxes, that are generally used in the antiperspirant emulsion compositions. To vary hardness of the antiperspirant emulsion compositions, the amount and type of wax present in the antiperspirant composition may require modification, thus requiring extensive efforts to maintain other similar characteristics between the various forms of the antiperspirant emulsion compositions, such as antiperspirant efficacy, appearance, and scent, while only modifying the hardness of the antiperspirant emulsion compositions.

Accordingly, it is desirable to provide processes for making antiperspirant emulsion compositions that enable hardness of the antiperspirant emulsion compositions to be modified without requiring formulary modification of the antiperspirant emulsion compositions. It is also desirable to provide antiperspirant emulsion compositions made by the processes and having a lower hardness than what would ordinarily be achieved with the antiperspirant emulsion compositions when made in accordance with traditional processes. It is also desirable to provide antiperspirant emulsion compositions having a low hardness. Furthermore, other desirable features and characteristics of the present invention will become apparent from the subsequent detailed description of the invention and the appended claims, taken in conjunction with the accompanying drawings and this background of the invention.

BRIEF SUMMARY

Processes for making an antiperspirant emulsion composition and antiperspirant emulsion compositions are provided herein. In an embodiment, a process for making an antiperspirant emulsion composition includes combining water and an antiperspirant active component to form a water phase. A hydrophobic carrier and a structurant are combined to form an oil phase. The structurant has a melting point above ambient temperature. The oil phase is heated to a first temperature of at least a melting point of the structurant that is disposed in the oil phase. The water phase and the heated oil phase are mixed to form the antiperspirant emulsion composition. The antiperspirant emulsion composition is cooled under continued mixing.

In another embodiment, an antiperspirant emulsion composition is made by a process that includes combining water and an antiperspirant active component to form a water phase. A hydrophobic carrier and a structurant are combined to form an oil phase. The structurant has a melting point above ambient temperature. The oil phase is heated to a first temperature of at least a melting point of the structurant that is disposed in the oil phase. The water phase and the heated oil phase are mixed to form the antiperspirant emulsion composition. The antiperspirant emulsion composition is cooled under continued mixing.

In another embodiment, an antiperspirant emulsion composition includes a water phase and an oil phase. The water phase is present in an amount of from about 60 to about 85 weight %, based upon the total weight of the antiperspirant emulsion composition and the oil phase is present in an amount of from about 15 to about 40 weight %, based upon the total weight of the antiperspirant emulsion composition. The water phase includes an antiperspirant active component present in the water phase in an amount of from about 10 to about 90 weight %, based upon the total weight of the water phase. The oil phase includes a hydrophobic carrier present in an amount of from about 30 to about 80 weight %, based upon the total weight of the oil phase, and a structurant present in an amount of from about 20 to about 60 weight %, based upon the total weight of the oil phase. The antiperspirant emulsion composition has a hardness of less than or equal to about 150 grams force.

BRIEF DESCRIPTION OF THE DRAWINGS

The present invention will hereinafter be described in conjunction with the following drawing figures, wherein like numerals denote like elements, and wherein:

FIG. 1 is a graph showing a relationship between cooling temperatures and resulting hardness of reference antiperspirant emulsion compositions in accordance with an embodiment when the antiperspirant emulsion compositions are continually mixed, with mixing ceasing at the particular cooling temperature.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Processes for making an antiperspirant emulsion composition, antiperspirant emulsion compositions made by the processes, and antiperspirant emulsion compositions having low hardness are provided herein. In particular, the antiperspirant emulsion compositions include a water phase and an oil phase and are made by heating the oil phase and mixing the water phase and heated oil phase, as described in further detail below. Notably, in an embodiment, the processes for making the antiperspirant emulsion composition involve cooling the antiperspirant emulsion composition under continued mixing, which unexpectedly lowers a hardness of the antiperspirant emulsion compositions as compared to known processes that simply involve packaging the antiperspirant emulsion compositions while cooling without continued mixing. As a result, antiperspirant emulsion compositions having identical formulations can be made with varying hardness depending upon when mixing of the antiperspirant emulsion composition is ceased during cooling. Because varying hardness of antiperspirant emulsion compositions having identical formulations can be achieved in accordance with the processes described herein, diverse forms of antiperspirant emulsion compositions, ranging from solid stick forms to soft solids and creams, can be attained while substantially maintaining other similar characteristics, such as antiperspirant efficacy, appearance, and scent.

As alluded to above, the antiperspirant emulsion composition includes a water phase and an oil phase. For example, the antiperspirant emulsion composition may be a water-in-oil emulsion comprising the water phase mixed with the oil phase, in which the water phase is added to the oil phase during preparation of the antiperspirant emulsion composition. In one embodiment, the antiperspirant emulsion compositions includes the water phase present in an amount of from about 60 to about 85 weight %, such as from about 60 to about 75 weight %, based upon the total weight of the antiperspirant emulsion composition. In this embodiment, the oil phase is present in an amount of from about 15 to about 40 weight %, such as from about 25 to about 40 weight %, based upon the total weight of the antiperspirant emulsion composition.

The water phase includes water and an antiperspirant active component. The antiperspirant active component, being present in the water phase, is water soluble and includes an antiperspirant active compound. In one exemplary embodiment, the water phase comprises a water-soluble antiperspirant active compound. The antiperspirant active compound may be based upon an astringent metal salt. By "based upon", it is meant that the antiperspirant active compound is either an astringent metallic salt, or is derived from an astringent metallic salt (such as a complex of an astringent metallic salt, buffer, and water). Without being bound to any particular theory, it is believe that antiperspirant active compounds reduce sweating by diffusing through the sweat ducts of apocrine glands (sweat glands responsible for body odor) and hydrolyzing in the sweat ducts, where they combine with proteins to form an amorphous metal hydroxide agglomerate, plugging the sweat ducts so sweat cannot diffuse to the skin surface. The antiperspirant active component generally may be a commercial product and may contain additional compounds beyond the antiperspirant active compound as known in the art, such as a buffer (in addition to any buffer that may be bound to the antiperspirant active compounds), calcium chloride, and water.

Antiperspirant active compounds based upon astringent metallic salts are known in the art. Suitable antiperspirant active compounds may include inorganic and organic astringent metallic salts, especially inorganic and organic salts of aluminum, zirconium, and zinc, as well as mixtures thereof. More specific suitable antiperspirant active compounds include aluminum-containing and/or zirconium-containing salts or materials, such as aluminum halides, aluminum chlorohydrates, aluminum hydroxyhalides, zirconyl oxyhalides, zirconyl hydroxyhalides, and mixtures thereof. Exemplary aluminum salts include those having the general formula $Al_2(OH)_aCl_b$ x $(H_2O)$, wherein a is from 2 to about 5; the sum of a and b is about 6; x is from about 1 to about 6; and wherein a, b, and x may have non-integer values. Exemplary zirconium salts include those having the general formula $ZrO(OH)_{2-a}Cl_a$ x $(H_2O)$, wherein a is from about 1.5 to about 1.87, x is from about 1 to about 7, and wherein a and x may both have non-integer values. In an embodiment, the antiperspirant active compound includes zirconium salt complexes that additionally contain aluminum and glycine, commonly known as ZAG complexes. These ZAG complexes contain aluminum chlorohydroxide and zironyl hyroxy chloride conforming to the above-described formulas. Examples of antiperspirant active compounds suitable for use in the various embodiments contemplated herein include aluminum dichlorohydrate, aluminum-zirconium octachlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum-zirconium trichlorohydrate, aluminum zirconium tetrachlorohydrate, aluminum zirconium pentachiorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, zirconium chlorohydrate, aluminum chloride, aluminum sulfate buffered, and the like, and mixtures thereof. Aluminum zirconium octachlorohydrex glycine complexes are commercially available, for example, from Summit Reheis under the designation AAZG-3109.

The antiperspirant active compound is present in the antiperspirant emulsion composition in an amount that provides a measurable antiperspirant effect when applied to the underarms of a consumer. In an embodiment, the antiperspirant active compound is present in an amount of from about 10 to about 25 weight % (USP), such as from about 14 to about 20 weight % (USP), based on the total weight of the antiperspirant emulsion composition. As used herein, weight % (USP) of an antiperspirant compound is calculated as anhydrous weight percent in accordance with the U.S.P. method, as is known in the art. This calculation excludes any bound water and buffer such as glycine. It is to be appreciated that most commercially available antiperspirant active compounds are sold in mixtures along with other compounds that are not considered antiperspirant active compounds, such as water and buffer as described above in the context of the antiperspirant active component, and the above values do not account for the presence of such non-active compounds that may be present in the antiperspirant active component. In an embodiment, the antiperspirant active component includes antiperspirant active compounds in an amount of from about 20 to about 99 weight %, such as from about 20 to about 85 weight %, based on the total weight of the antiperspirant active component. Within the water phase, in an embodiment, the antiperspirant active component is present in the water phase in an amount of from about 10 to about 90 weight %, based upon the total weight of the water phase. It is to be appreciated that the amount of antiperspirant active component present in the water phase may be dependent upon the amount of antiperspirant active compound present in the antiperspirant active component and may also be dependent upon the amount of water phase present in the antiperspirant emulsion composition, with the amount of the antiperspirant active component in the water phase chosen to achieve a desired amount of antiperspirant active compound within the antiperspirant emulsion composition.

The water phase may also include additional optional components that serve a particular purpose. For example, in an embodiment, the water phase includes at least one water soluble carrier/solubilizer present in a sufficient amount to solubilize or disperse the water phase components of the antiperspirant emulsion composition. Such carriers/solubilizers suitable for use in the antiperspirant product include, but are not limited to, propylene glycol, glycerol, dipropyl glycol, ethylene glycol, butylene glycol, propylene carbonate, dimethyl isosorbide, hexylene glycol, ethanol, n-butyl alcohol, n-propyl alcohol, isopropyl alcohol, and the like. An additional structurant may also be present in the water phase as described in further detail below.

The oil phase includes a structurant and may include a combination of structurants. The structurant influences hardness and consistency of the antiperspirant emulsion composition. As referred to herein, the structurant also encompasses compounds known in the art as gellants. Although the structurant is present in the oil phase, an additional structurant may also be present in the water phase, as alluded to above, such that structurants may be present in both the oil phase and the water phase. The structurant present in the oil phase and the additional structurant present in the water phase may be the same or different.

The structurant has a melting point above ambient temperature. In an embodiment, the structurant has a melting point within a range of from about 50 to about 100° C., such as from about 70 to about 100° C., at ambient pressure. In particular, all structurants that are present in the antiperspirant emulsion composition may have a melting point within the above range, which serves to provide structure to the antiperspirant emulsion compositions at normal storage and usage temperatures that are generally near ambient temperature. The structurant and the additional structurant may be naturally-occurring or synthetic waxy materials, and the antiperspirant emulsion composition can include a combination of such structurants. Examples of suitable waxy materials include, but are not limited to, fatty alcohols that are solid at room temperature, hydrocarbon waxes, and silicone waxes. Such structurants are widely available, and by selection of the particular structurants themselves and their concentrations in the antiperspirant emulsion composition, it is possible to influence the hardness and consistency of the antiperspirant emulsion composition.

In a specific embodiment, a high molecular weight (MW) polyethylene is employed as a structurant. As used herein, the term "high molecular weight polyethylene" or "high MW polyethylene" refers to polyethylene having a molecular weight of from about 200 to about 5000 Daltons (Da). Also in this embodiment, when high MW polyethylene is used in the oil phase as a structurant, the oil phase may also include at least one low MW synthetic wax (i.e., synthetic wax having a molecular weight in the range of 1200-2900 Da) as another structurant. In addition to facilitating the high MW polyethylene by serving a structurant function, the low MW synthetic wax also improves the manufacturing processes of the antiperspirant emulsion compositions. Generally, high MW polyethylene has a relatively high melting point (70-100° C.) which may require higher melting temperatures at which the oil phase is to be heated to melt the high MW polyethylene. However, the presence of an effective amount of low MW synthetic wax modifies the high MW polyethylene, thus lowering the effective melting point of the high MW polyethylene. In an exemplary embodiment, the low MW synthetic wax is present in the oil phase in an amount of about 0.01 to about 3 weight %, based upon the total weight of the oil phase.

In an embodiment, a total amount of all structurants included in the antiperspirant emulsion composition is from about 10 to about 30 weight %, such as from about 10 to about 20 weight %, based upon the total weight of the antiperspirant emulsion composition. Within the oil phase, in particular, a total amount of structurants present therein may be from about 20 to about 60 weight %, such as from about 30 to about 50 weight %, based upon the total weight of the oil phase.

The oil phase further includes a hydrophobic carrier and may include a combination of hydrophobic carriers. Examples of suitable hydrophobic carriers include liquid siloxanes and volatile polyorganosiloxanes. By "volatile", it is meant that the materials have a measurable vapor pressure at ambient conditions. The volatile polyorganosiloxanes can be linear, cyclic, or mixtures thereof. The linear volatile polyorganosiloxanes generally have viscosities of less than about 5 centistokes at 25° C., while the cyclic volatile polyorganosiloxanes have viscosities under 10 centistokes at 25° C. Specific examples of volatile polyorganosiloxanes include cyclomethicones, which have from about 3 to about 6 silicon atoms, such as cyclotetramethicone, cyclopentamethicone, and cyclohexamethicone, and mixtures thereof. The hydrophobic carrier may also include, in addition to or as an alternative to the liquid siloxanes and volatile polyorganosiloxanes, nonvolatile silicones such as dimethicone and dimethicone copolyols, which have from about 2 to about 9 silicon atoms. Examples of suitable dimethicone and dimethicone copolyols include polyalkyl siloxanes, polyalkylaryl siloxanes, and polyether siloxane copolymers. In an embodiment, the hydrophobic carrier is present in an amount of from about 30 to about 80 weight %, such as from about 30 to about 50 weight %, based upon the total weight of the oil phase.

It is to be appreciated that additives other than the components mentioned above may also be included in the antiperspirant emulsion compositions contemplated herein. The additives may include any of those used in conventional antiperspirant emulsion compositions. For example, the antiperspirant composition may include additives that cause the antiperspirant composition to exhibit long-lasting fragrance, odor protection, bacteria control, and/or another desired purpose and/or function. These additives include, but are not limited to, fragrances, including encapsulated fragrances, dyes, pigments, preservatives, antioxidants, skin conditioning agents such as moisturizers, and the like. Another class of additives includes high refractive index compounds. The optional additives can be included in the antiperspirant composition in an amount of 0 to about 20 weight %.

In an exemplary embodiment, a method for making an antiperspirant emulsion composition contemplated herein includes combining water and the antiperspirant active component to form a water phase. For example, the water and antiperspirant active component, as well as additional components to be introduced into the antiperspirant emulsion composition through the water phase, can be mixed in a vessel using sufficient agitation to prepare the water phase as a homogeneous mixture. During formation of the water phase or after the water phase is formed, the water phase may be heated. For example, in an embodiment, the water phase may be heated to a water phase temperature in a range of from about 70 to about 90° C., such as from about 75 to about 85° C. However, it is to be appreciated that heating the water phase is optional, especially if no waxes or other components are included therein that require melting to form a homogeneous mixture.

Before, during, or after formation of the water phase, the hydrophobic carrier and structurant are combined to form the oil phase. For example, the hydrophobic carrier and structurant, as well as additional components to be introduced into the antiperspirant emulsion composition through the oil phase, can be mixed in a vessel separate from the water phase. During formation of the oil phase, or after the oil phase is formed, the oil phase is heated to a first temperature of at least a melting point of the structurant that is disposed in the oil phase, which is sufficiently high to melt the structurant but is not so high as to burn or discolor the structurant. When a combination of structurants is included in the oil phase, the first temperature is at least equal to the highest melting point of any of the structurants. As such, the oil phase may be heated for a sufficient amount of time to melt the structurant and allow the oil phase to be homogeneously formed. In one embodiment, the first temperature is in the range of from about 50 to about 100° C., such as from about 70 to about 100° C.

After forming the oil phase, the water phase and the heated oil phase are mixed to form the antiperspirant emulsion composition. Mixing can be performed, for example, using a Lightnin®, IKA®, Scott Turbon, or Ross mixer. In an embodiment, the water phase and the heated oil phase are mixed at the first temperature at which the oil phase is heated to melt the structurant. In another embodiment, the water phase and the heated oil phase are mixed at a mixing temperature of at least the melting point of the structurant, with the mixing temperature being different from the first temperature at which the oil phase is heated to melt the structurant. In another embodiment, the oil phase may be cooled to a temperature that is less than a melting point of the structurant so long as the oil phase remains flowable. In the embodiment in which the oil phase is cooled, heating of the oil phase may cease prior to mixing the water phase and the oil phase, which allows the oil phase to slightly cool prior to mixing with the water phase. For example, the oil phase may be allowed to cool to a mixing temperature of from about 75 to about 90° C., while under continued mixing. The oil phase and the water phase may be mixed using any known method to form a water-in-oil emulsion. In an embodiment, the water phase is transferred to the oil phase via droplet to form an emulsion, keeping both separated phases mixing and at the same mixing temperatures, such as from about 75 to about 90° C. Once the water phase is fully transferred to the oil phase, the antiperspirant emulsion composition is continually mixed for a time sufficient to stabilize the antiperspirant emulsion composition. In one embodiment, mixing at the mixing temperature is continued for about 10 minutes. Additional optional components, such as fragrance, may be added to complete the antiperspirant emulsion composition.

After mixing the water phase and the oil phase to form the antiperspirant emulsion composition, the antiperspirant emulsion composition is cooled under continued mixing, which differs from conventional processes that generally cease mixing upon commencement of cooling. The cooling step referred to herein applies to the final antiperspirant emulsion composition after all components have been included therein. Mixing can be performed using a dedicated mixer, such as the mixer that is used to mix the water phase and the oil phase, and the continued mixing as referred to herein excludes natural mixing that may occur through pouring of the antiperspirant emulsion composition. In an embodiment, mixing is performed at a range of from about 200 to about 500 rpm, such as from about 300 to about 400 rpm, using the Lightnin®, IKA®, Scott Turbon, or Ross mixer. Whereas conventional processes generally involve pouring the antiperspirant emulsion compositions into suitable molds prior to cooling (to take advantage of flowability of the antiperspirant emulsion compositions prior to solidification upon cooling), the instant process involves continued mixing upon cooling. By continuing to mix the antiperspirant emulsion composition during cooling, hardness of the antiperspirant emulsion composition can be modified, as set forth above, without changing the formulation of the antiperspirant emulsion composition. Without being bound by any particular theory, it is believe that during cooling of the antiperspirant emulsion composition without continued mixing, an organized lattice is formed within the antiperspirant emulsion composition due to the presence of the structurant. By continuing to mix that antiperspirant emulsion composition during cooling, it is believed that the formation of the organized lattice is disturbed, resulting in a lower hardness of the antiperspirant emulsion composition as compared to known processes that simply involve packaging the antiperspirant emulsion compositions while cooling without continued mixing. Depending upon a particular cooling temperature to which the antiperspirant emulsion composition is cooled when mixing of the antiperspirant emulsion composition is ceased, hardness of the resulting antiperspirant emulsion composition can be varied.

In an embodiment, the antiperspirant emulsion composition is cooled to a predetermined cooling temperature below a pour point of the antiperspirant emulsion composition under continued mixing. The pour point, as referred to herein, is the temperature at which the antiperspirant emulsion composition becomes flowable, which enables the antiperspirant emulsion composition to be poured. In an embodiment, the pour point may be a melting point of the structurant. However, it is to be appreciated that, due to the presence of the hydrophobic carrier, water, and other components in the antiperspirant emulsion composition, the antiperspirant emulsion composition may still flow at temperatures lower than a melting point of the antiperspirant emulsion composition. Cooling the antiperspirant emulsion composition to the cooling temperature below the pour point generally results in the largest drop in hardness of the antiperspirant emulsion composition, as compared to cooling without continued mixing. For example, as shown in FIG. 1, hardness may be decreased by a value of from about 50% to about 80%, based upon comparison of hardness in grams force (gf), simply by continuing to mix the antiperspirant emulsion composition while cooling the antiperspirant emulsion composition to the cooling temperature that is below the pour point. Of course, actual differences in hardness are dependent upon the particular formulation of the antiperspirant emulsion composition. In an embodiment, the cooling temperature is below the pour point but above ambient temperature, and mixing is ceased prior to further cooling of the antiperspirant emulsion composition to ambient temperature. In another embodiment, the cooling temperature is ambient temperature and the antiperspirant emulsion composition is continually mixed until cooling the antiperspirant emulsion composition to ambient temperature, under which circumstance hardness of the antiperspirant emulsion composition can be minimized. Depending upon when mixing is ceased during cooling, the antiperspirant emulsion composition may have a consistency ranging from a soft, non-flowing, solid composition that can be rubbed or wiped across the skin, to a gel, cream, or lotion consistency.

In an embodiment, the antiperspirant emulsion composition is a soft solid, cream, or lotion having a hardness of less than or equal to about 150 gf, such as less than or equal to about 100 gf or from about 8 to about 55 gf, as measured by a TA.XT2i Texture Analyzer at the following settings: pre-speed—1.0 millimeters/second (mm/s); trigger force—5.0 grams (g); test speed—1.0 mm/s; retraction speed—5 0 mm/s; distance—5.0 mm; and cycles—1. The TA.XT2i is manufactured by Stable Micro Systems Ltd. of the United Kingdom. The aforementioned hardnesses in the antiperspirant emulsion composition can be achieved through making the antiperspirant emulsion composition in accordance with the processes described above that include continued mixing of the antiperspirant emulsion composition during cooling. When the antiperspirant emulsion composition has the hardness of less than about 100 gf, such as from about 8 to about 55 gf, the antiperspirant emulsion composition may be extrudable and, thus, may be considered a soft solid antiperspirant emulsion composition.

The following Examples are to be read as illustrative of the antiperspirant compositions contemplated herein and method of making the same as described herein, and are not to be interpreted as limiting.

EXAMPLE

An example of an antiperspirant emulsion composition was prepared as a water-in-oil emulsion to illustrate the effect of continued mixing while cooling the emulsion on resulting hardness of the emulsion. Table I provides the types and amounts of each component included within the example of the antiperspirant emulsion composition, with all amounts in weight % based upon the total weight of the antiperspirant emulsion composition. To prepare the example of the antiperspirant emulsion composition, all components of the water phase were combined and heated at a temperature of about 84.3° C. under mixing at about 200 rpm using a Lightnin® mixer. All components of the oil phase were separately mixed from the water phase and heated to a temperature of about 93.5° C. under mixing at about 200 rpm using a Lightnin® mixer for a sufficient duration to visibly melt all structurant present in the oil phase. The oil phase was cooled to a temperature of about 87.2° C., at which temperature the oil phase was still flowable. The water phase was then mixed with the oil phase by introducing the water phase into the oil phase with an initial mixing speed of about 200 rpm with incremental increases to 400 rpm. Fragrance was added to complete the antiperspirant emulsion composition, and the antiperspirant emulsion composition was continually mixed at a temperature of about 84.2° C. for about 10 minutes to form a microscopically homogeneous emulsion prior to commencement of cooling. Various trial runs were performed in which the antiperspirant emulsion composition was cooled to different cooling temperatures under continued mixing, with mixing ceasing once the cooling temperature was reached. Table II provides cooling temperatures and resulting hardness of the antiperspirant emulsion compositions, in grams force (gf), as measured by a TA.XT2i Texture Analyzer at the following settings: pre-speed—1.0 millimeters/second (mm/s); trigger force—5.0 grams (g); test speed—1.0 mm/s; retraction speed—5.0 mm/s; distance—5.0 mm; and cycles—1. FIG. 1 graphically illustrates the data of Table II.

TABLE I

| | | Antipers. Emulsion Comp. |
|---|---|---|
| Water Phase | Water | 3.38 |
| | Antiperspirant Active Component | 59.60 |
| | PEG | 2.50 |
| | PPG | 2.50 |
| Oil Phase | Silicone | 12.17 |
| | Alkyl Benzoate | 8.00 |
| | Emulsifier | 1.25 |
| | Wax A | 10.50 |
| | Wax B | 0.10 |
| Total | | 100.00 |

Antiperspirant Active Component is a mixture of an aluminum and zirconium halide salt, glycine, and water, with a % activity of about 29.2%.

PEG is a polyethylene glycol having a number average molecular weight of from about 380 to about 420 Daltons.

PPG is a polypropylene glycol having a number average molecular weight of about 1000 Daltons.

Silicone is a cyclohexasiloxane.

Alkyl Benzoate is a C12-15 alkyl benzoate.

Emulsifier is a cetyl PEG/PPG-10/1 dimethicone emulsifier.

Wax A is polyethylene wax having a number average molecular weight of from about 450 to about 500 Daltons.

Wax B is a synthetic wax having a number average molecular weight of from about 1500 to about 2000 Daltons.

TABLE II

| Cooling Temp., ° C. | Hardness, gf |
|---|---|
| 92.5 | 180 |
| 89.5 | 175 |
| 85 | 185 |
| 82 | 195 |
| 80 | 48 |
| 78 | 50 |
| 60 | 18 |
| 55 | 10 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for making an antiperspirant emulsion composition, the process comprising the steps of:
   combining water and an antiperspirant active component to form a water phase;
   combining a hydrophobic carrier and a structurant to form an oil phase, the structurant having a melting point above ambient temperature;
   heating the oil phase to a first temperature of at least a melting point of the structurant disposed therein;

mixing the water phase and the heated oil phase at a mixing temperature of at least the melting point of the structurant and different from the first temperature to form the antiperspirant emulsion composition; and cooling the antiperspirant emulsion composition under continued mixing wherein the antiperspirant emulsion composition is cooled to a cooling temperature below a pour point of the antiperspirant emulsion composition under continued mixing.

2. The process of claim 1, wherein the cooling temperature is ambient temperature.

3. The process of claim 1, wherein the cooling temperature is above ambient temperature, and wherein mixing is ceased prior to further cooling to ambient temperature.

4. The process of claim 1, wherein the structurant has a melting point within a range of from about 50 to about 100° C.

5. The process of claim 1, wherein the water phase is present in the antiperspirant emulsion composition in an amount of from about 60 to about 85 weight % and the oil phase is present in the antiperspirant emulsion composition in an amount of from about 15 to about 40 weight %, both based upon the total weight of the antiperspirant emulsion composition.

6. The process of claim 5 wherein the antiperspirant active component is present in the water phase in an amount of from about 10 to about 90 weight %, based upon the total weight of the water phase.

7. The process of claim 5 wherein the structurant is present in the oil phase in an amount of from about 20 to about 60 weight %, based upon the total weight of the oil phase.

8. The process of claim 1, wherein the water phase further comprises an additional structurant.

9. The process of claim 1, wherein the antiperspirant emulsion composition has a hardness of less than or equal to about 150 grams force.

10. An antiperspirant emulsion composition made by a process comprising the steps of:
combining water and an antiperspirant active component to form a water phase;
combining a hydrophobic carrier and a structurant to form an oil phase, the structurant having a melting point above ambient temperature;
heating said oil phase to a first temperature of at least a melting point of said structurant disposed therein;
mixing said water phase and said heated oil phase at a mixing temperature of at least the melting point of the structurant and different from the first temperature to form said antiperspirant emulsion composition; and
cooling said antiperspirant emulsion composition under continued mixing; wherein the antiperspirant emulsion composition is cooled to a cooling temperature below a pour point of the antiperspirant emulsion composition under continued mixing.

11. The antiperspirant emulsion composition of claim 10, wherein said structurant has a melting point within a range of from about 50 to about 100° C.

12. The antiperspirant emulsion composition of claim 10, wherein said water phase is present in said antiperspirant emulsion composition in an amount of from about 60 to about 85 weight % and said oil phase is present in said antiperspirant emulsion composition in an amount of from about 15 to about 40 weight %, both based upon the total weight of said antiperspirant emulsion composition.

13. The antiperspirant emulsion composition of claim 12 wherein said antiperspirant active component is present in said water phase in an amount of from about 10 to about 90 weight %, based upon the total weight of said water phase.

14. The antiperspirant emulsion composition of claim 12, wherein said structurant is present in said oil phase in an amount of from about 20 to about 60 weight %, based upon the total weight of said oil phase.

15. The antiperspirant emulsion composition of claim 10, wherein said water phase further comprises an additional structurant.

16. The antiperspirant emulsion composition of claim 10 having a hardness of less than or equal to about 150 grams force.

* * * * *